United States Patent [19]

Cohen

[11] Patent Number: 4,605,960

[45] Date of Patent: Aug. 12, 1986

[54] METHOD FOR AVOIDING IDENTIFYING PERIMETER VARIATIONS AS BLEMISHES IN A CCD IMAGE

[75] Inventor: Edward Cohen, Lancaster, Pa.

[73] Assignee: RCA Corporation, Princeton, N.J.

[21] Appl. No.: 663,699

[22] Filed: Oct. 22, 1984

[51] Int. Cl.[4] ............................................. H04N 7/18
[52] U.S. Cl. .................................................... 358/106
[58] Field of Search ............... 358/213, 212, 106, 209, 358/139, 10, 163; 382/8

[56] References Cited

U.S. PATENT DOCUMENTS 4,454,545 6/1984 Duschl ................................ 358/213

FOREIGN PATENT DOCUMENTS

2102122 1/1983 United Kingdom ................ 358/106

Primary Examiner—Gene Z. Rubinson
Assistant Examiner—Stephen Brinich
Attorney, Agent, or Firm—E. M. Whitacre; D. H. Irlbeck; L. L. Hallacher

[57] ABSTRACT

The identification of permissible variations in a CCD image perimeter as blemishes is avoided by sequentially considering the adjacent pixels of a selected plurality of pixels. Pixel motions are defined between adjacent pixels and can be either straight or diagonal. Diagonal pixel motions are recorded as straight when the first and last pixel motions are diagonal in opposite directions and the intervening pixel motions are straight.

19 Claims, 19 Drawing Figures

METHOD FOR AVOIDING IDENTIFYING PERIMETER VARIATIONS AS BLEMISHES IN A CCD IMAGE

BACKGROUND

This invention relates generally to CCD (charge coupled device) imaging and particularly to a method for avoiding the identification of perimeter variations as blemishes in the proximity of the perimeter of an image on a CCD.

U.S. Pat. No. 4,454,545 issued to R. A. Duschl discloses a CCD based inspection system.

U.S. Pat. No. 4,575,751 entitled "Method and Subsystem for Plotting the Perimeter of an Object" issued to R. A. Duschl now U.S. Pat. No. 4,575,751 discloses a system for plotting the perimeter of an image cast onto a CCD. The image pixels immediately adjacent to the perimeter pixels are identified and their addresses held in memory irrespective of the orientation of the image and the size of the image.

U.S. application Ser. No. 663,153 entitled "Method For Detecting Blemishes Near The Perimeter Of A CCD Image" filed on even date herewith by Edward Cohen, discloses a method for detecting blemishes in the proximity of a perimeter plotted by the system disclosed in R. A. Duschl U.S. Pat. No. 4,575,751.

These disclosures are incorporated herein by reference.

The systems described in the above-referenced applications and patent are quite satisfactory for the purposes intended. However, difficulties sometime arise because the perimeters being plotted are not perfectly straight and thus do not perfectly lie along the rows or columns of the CCD. Instead, the perimeters typically vary across several rows or columns of pixels. The method described in application Ser. No. 663,153 detects blemishes in the proximity of the perimeter. However, in some instances permissible perimeter variations can be identified as blemishes and acceptable perimeters can be rejected. For this reason, there is a need for a method for distinguishing permissible perimeter variations from blemishes in the close proximity of the perimeter of an object cast onto a CCD. The instant invention fulfills this long felt need.

The present invention is cast into the environment of detecting the perimeter of a black matrix on the inside surface of a CRT faceplate panel. This environment was selected when describing the present invention because the invention is an improvement of the inventions described in the referenced patent and patent applications and those inventions are described in that environment. Nevertheless it will be understood by those skilled in the art that the present invention is useful in distinguishing permissible perimeter variations from blemishes in the proximity of the perimeter of any image cast onto a CCD.

SUMMARY

A method of avoiding the identification of permissible variations in the perimeter of an image on a CCD (charge coupled device) as blemishes in the proximity of the perimeter includes defining the consideration of adjacent perimeter identifying pixels as pixel motions. Adjacent pixels are pixels having contiguous sides or contiguous corners. In a pixel direction matrix, the pixel under consideration is surrounded by adjacent pixels whereby side contiguous pixels result in straight pixel motions and corner adjacent pixels result in diagonal pixel motions. A plurality of adjacent pixels is sequentially considered and diagonal pixel motions are recorded as straight pixel motions where the first and last pixel motions are diagonal in opposite directions and all intervening pixel motions are straight.

DETAILED DESCRIPTION

Figure 1:
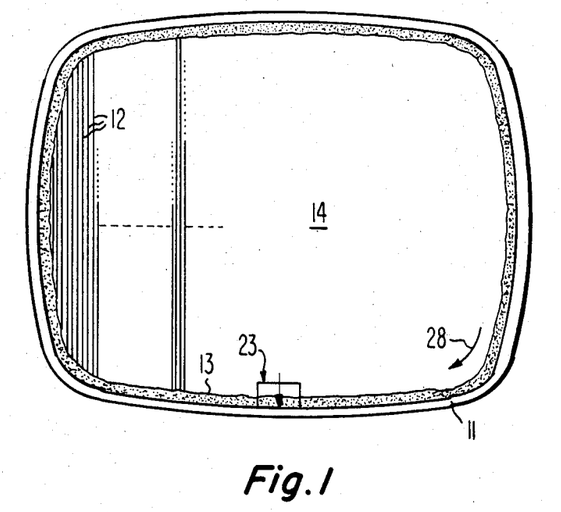
FIG. 1 shows the perimeter of the black matrix present on the inside surface of a faceplate panel.

In FIG. 1, the inside surface of a CRT faceplate panel 11 includes a black matrix which is composed of a plurality of parallel black lines 12 and a perimeter 13. The parallel lines 12 extend across the entire surface of the panel 11 and only several are shown for simplicity. Phosphors are arranged in the spaces between the matrix lines 12 in a sequential fashion and each phosphor emits a different color of light when impacted with electrons. Thus, the phosphors are arranged in a repetitive pattern such as red, green and blue across the entire inside surface of the panel 11 to form a screen 14.

Figure 2:
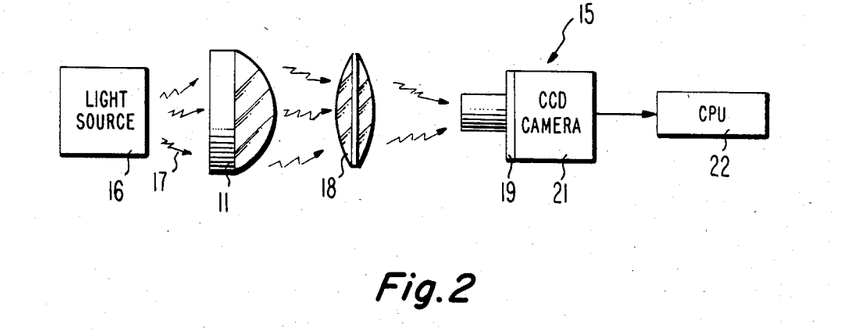
FIG. 2 is a simplified showing of a CCD based image inspection system.

FIG. 2 shows a CCD based inspection system 15 which can be of the type described in U.S. Pat. No. 4,454,545. The inspection system 15 includes a light source 16 the light rays 17 of which fully illuminate the phosphor screen 14 on the inside surface of the panel 11. The light rays 17 pass through the phosphor screen and are focused by a lens 18 onto the CCD 19 within a CCD camera 21. Each pixel of the CCD 19 in the camera 21 is charged to a particular level depending upon the amount of light received by the individual pixels. Thus, the pixels receiving light passing through the screen 14 are charged to a different level than the pixels shaded by the perimeter 13. The pixel data are transferred from the CCD 19 to a central processing unit 22 and processed in accordance with the inspection being made. The inspection can be the detection of blemishes in the screen 14 as described in U.S. Pat. No. 4,454,545 while utilizing the perimeter plotting described in the above-referenced U.S. Pat. No. 4,575,751 The detection of blemishes in the proximity of the perimeter 13 described in the above-referenced application Ser. No. 663,153 and the method of avoiding identifying permissible perimeter variations as blemishes described hereinafter also are carried out in the CPU 22.

Figure 3:
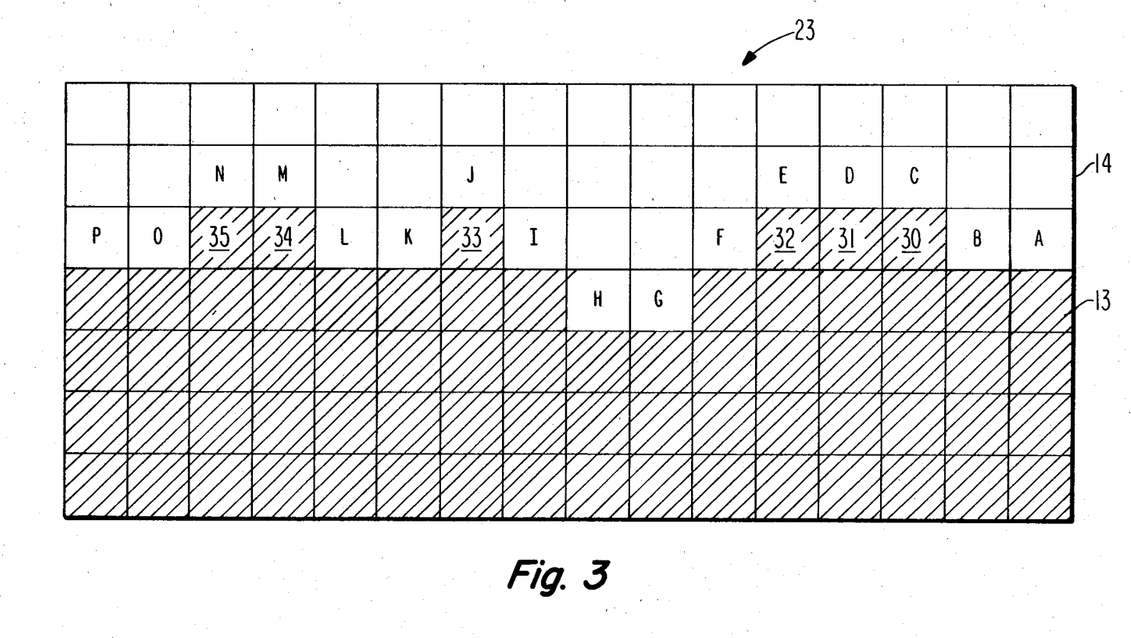
FIG. 3 is an enlarged portion of the black matrix perimeter of FIG. 1 showing how permissible perimeter variations can be erroneously detected as blemishes in the proximity of the perimeter.

FIG. 3 is a greatly magnified view of the rectangular portion 23 of the perimeter 13 of FIG. 1. In FIG. 3, the cross-hatched blocks represent pixels which are shaded by the perimeter 13. The clear blocks represent pixels receiving light through the phosphor screen 14. The pixels alphabetically labeled A-P represent the pixels which are identified as bordering the perimeter 13 utilizing the perimeter plotting described in U.S. Pat. No. 4,575,751. Application Ser. No. 663,153 describes a method of detecting blemishes in the proximity of the perimeter 13 to avoid the blemishes being identified as part of the perimeter 13. The identification of such perimeter blemishes is accomplished by sequentially considering the charge levels on the perimeter defining pixels while progressing around the perimeter 13 in a preselected direction identified by the arrow 28 in FIG. 1, where the preselected direction is selected to be clockwise. Adjacent pixels are defined as two pixels having contiguous sides or having contiguous corners and the consideration of three consecutive pixels defines a motion. The consideration of two adjacent pixels defines a pixel direction and two consecutive pixel directions define each motion direction. Accordingly, each motion direction can be straight, or can turn either clockwise or counterclockwise. Any number of clockwise turning motions or straight motions is acceptable but a blemish indication is provided upon the occurrence of two counterclockwise turning motions without an intervening clockwise turning motion. The pixel directions are provided to the CPU 22 and used to identify blemishes in the proximity of the perimeter 13 in a manner fully described in the application Ser. No. 663,153.

The system described in application Ser. No. 663,153 is satisfactory for the purposes intended. However, difficulties sometimes arise because the perimeter 13 (FIG. 1) cannot be made perfectly smooth. For example, as shown in FIG. 3, the perimeter 13 is somewhat widened at the pixels identified 30-35, also the perimeter is slightly narrow at the pixels G and H. Variations of the types shown by these pixels are permissible and thus should not be identified as blemishes in the proximity of the perimeter 13. When using the method described in application Ser. No. 663,153 consideration of pixels B, C, D of FIG. 3 results in a counterclockwise motion, consideration of pixels C, D, E results in a straight motion and consideration of pixels D, E, F results in a counterclockwise motion. Accordingly, in accordance with the criteria of the method described in application Ser. No. 663,153 the pixels 30, 31 and 32 would be identified as a blemish despite the fact that they are a permissible perimeter variation. Similarly, consideration of pixels L, M, N, O around the pixels 34 and 35 also would result in a blemish indication. The method described herein avoids these erroneous blemish indications and thus the hereindescribed method is executed prior to the execution of the blemish detection method described in application Ser. No. 663,153.

Figure 4:
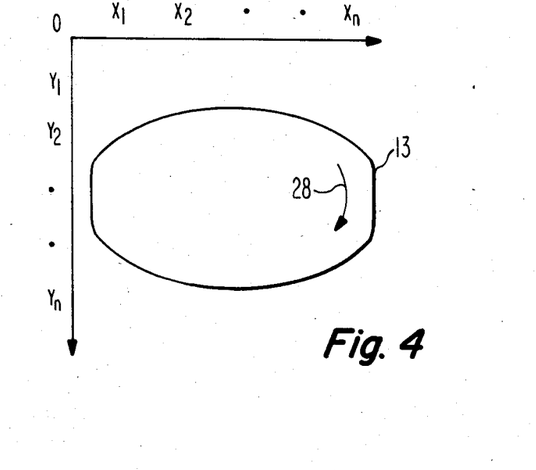
FIG. 4 shows the relationship of the X and Y axes with the perimeter and defines the directions of pixel consideration along the axes.

FIG. 4 shows that the entire perimeter 13 is positioned beneath the horizontal X axis and to the right of the vertical Y axis. Additionally, FIG. 4 shows that the X values increase moving to the right away from the origin O and the Y pixel values increase going downwardly away from the origin O.

Figure 5A:
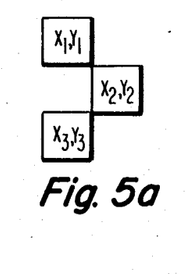
FIGS. 5a to 5f show several types of permissible variations which could be erroneously identified as blemishes, when considering the vertical, or Y, portions of the perimeter.
Figure 5B:
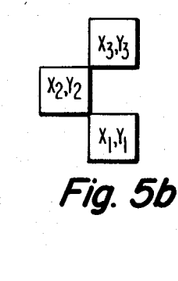
Figure 5C:
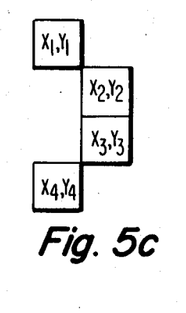
Figure 5D:
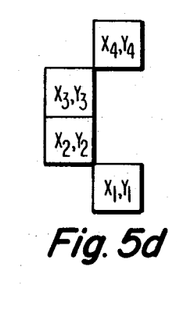
Figure 5E:
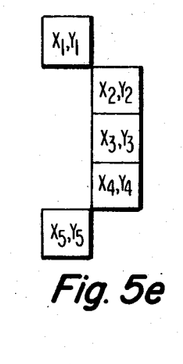
Figure 5F:
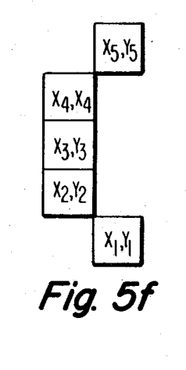
Figure 6A:
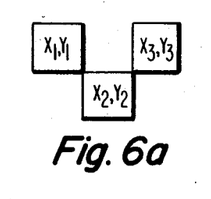
FIGS. 6a to 6f show several types of permissible variations which could be erroneously identified as blemishes when considering the horizontal, or X, portions of the perimeter.
Figure 6B:
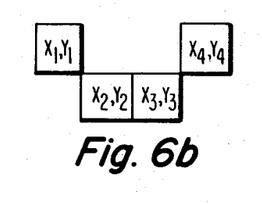
Figure 6C:
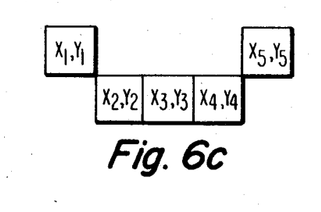
Figure 6D:
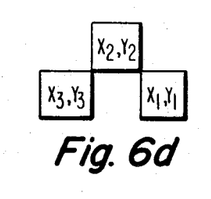

FIGS. 5a to FIG. 5f show several permissible perimeter variations which can be erroneously identified as perimeter boardering blemishes. Any of the variations shown in FIG. 5a to 5f can occur when moving downwardly along the right portion of the perimeter 13, as shown in FIG. 1, or when moving upwardly along the left portion of the perimeter 13. FIGS. 6a to 6f show permissible perimeter variations similar to those shown in FIGS. 5a to 5c but which can be encountered when moving horizontally, either right or left, along the top and bottom portions of the perimeter 13. In FIGS. 5a to 5f and 6a to 6f, the pixels labeled $X_1, Y_1$, are the first pixel considered in a group of pixels and those labeled $X_5, Y_5$ are the last pixel considered. Thus, FIGS. 5a, 5c and 5e represent downward motion while FIGS. 5b, 5d and 5f represent upward motion. Similarly, FIGS. 6a to 6c represent horizontal motion to the right and 6d to 6f to the left. However, these directions are exemplary only and any of the FIGS. 5a to 5f patterns can be encountered when going in either vertical direction, and any of the FIGS. 6a to 6f patterns can be encountered when going in either horizontal direction.

Figure 7:
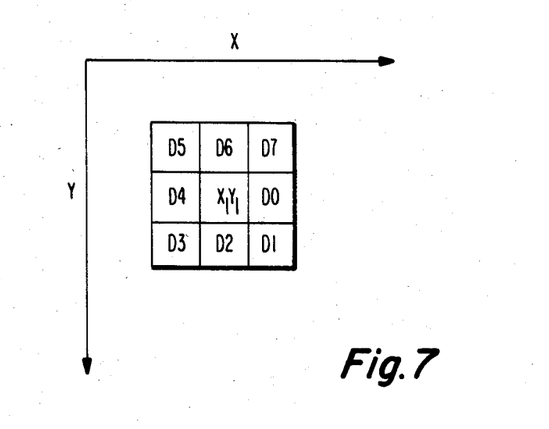
FIG. 7 shows how the pixel directions of the motions are defined.

FIG. 7 shows how the pixel directions which are provided to the CPU 22 are defined. These pixel motions are used to calculate the clockwise, counterclockwise and straight motion directions. In FIG. 7, the central pixel is identified $X_1, Y_1$ and thus is representative of the similarly identified pixels in FIGS. 5a and 5f and 6a to 6f. Assuming that pixel $X_1, Y_1$ of FIG. 7 corresponds to pixel F of FIG. 3, the next perimeter defining pixel is pixel G. Accordingly in accordance with FIG. 7, a D3 pixel motion would be provided to the CPU 22. The central pixel $X_1, Y_1$ corresponds to pixel G of FIG. 3 when determining the next pixel direction and because pixel H is immediately to the left of pixel G a D4 pixel direction is provided to the CPU 22. The D3 and D4 pixel motions are processed by the CPU 22 to provide a clockwise turning motion in accordance with the method described in application Ser. No. 663,153. Thus, the pixel motion defining matrix shown in FIG. 7 moves around the perimeter 13 as the central pixel $X_1, Y_1$ is sequentially changed to correspond to the various perimeter defining pixels of FIG. 3. The orientation of the matrix with respect to the horizontal (X) and vertical (Y) axes remains unchanged as the matrix moves around the perimeter 13.

Briefly stated, the method described herein identifies the permissible perimeter variations shown in FIGS. 5a to 5f and 6a to 6f by first comparing the horizontal, or X, locations of a selected plurality of consecutive pixels and then comparing the vertical, or Y, locations of the same pixels. When any of the permissible perimeter variations of FIGS. 5a to 5f and 6a to 6f are detected, the actual pixel directions are ignored and one of the pixel directions 0, 2, 4 or 6 of FIG. 7 is provided to the CPU 22. For example, assuming that the pixel configuration shown in FIG. 5a is encountered, the pixel motion from pixel to pixel is a D1 direction as shown in FIG. 7. Also, the consideration going from pixel $X_2, Y_2$ to pixel $X_3, Y_3$ is a D3 motion as shown in FIG. 7. When the pixel direction from $X_2, Y_2$ to $X_3, Y_3$ is calculated the $X_2, Y_2$ pixel serves as the central pixel $X_1, Y_1$ in the FIG. 7 matrix. That is, the matrix is shifted one pixel downwardly and to the right. Because the pixel arrangement of FIG. 5a is a permissible perimeter variation the actual D1 and D3 motions are ignored and two consecutive D2 motions are provided to the CPU 22.

Figure 8A:
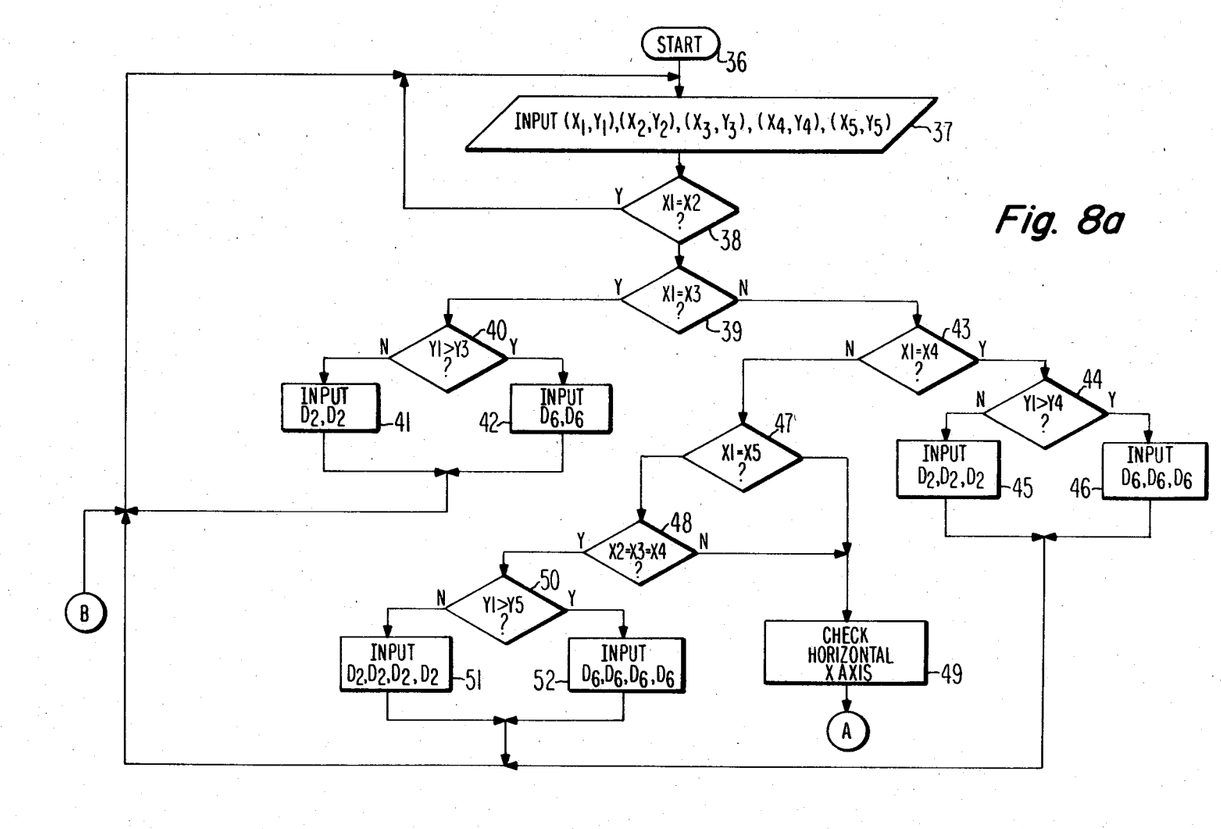
FIGS. 8a and 8b are a flow chart of a preferred method of distinguishing permissible perimeter variations from blemishes in the proximity of the perimeter.

FIG. 8a is a flow chart of a method when the pixels on the vertical right and left sides of the perimeter 13 are under consideration. The method starts at step 36 and at step 37 the addresses of the next five pixels to be considered are provided. The addresses of these five pixels have previously been made available to the CPU 22 by the perimeter plotting subsystem described in copending application Ser. No. 551,920. At step 38, the horizontal, or X, positions of the first two pixels are compared. When the horizontal position of these two pixels is the same, the pixels are vertically aligned and step 37 is returned to and the next succeeding pixel becomes the central pixel in the matrix of FIG. 7. In step 38 when the two pixels under consideration have different horizontal locations, step 39 is entered and the horizontal positions of the first and third pixels are compared. When the horizontal positions of the first and third pixels are the same, a pixel pattern similar to those shown in FIGS. 5a and 5b is indicated. Accordingly, step 40 is entered to compare the vertical positions of the first and third pixels. At step 40 when the first pixel considered is further from the X axis than the third pixel considered, the motion is upwardly along the left side of the perimeter 13 and two D6 motions are provided to the CPU 22 in accordance with the matrix of FIG. 7, rather than the actual D1 and D3 pixel motions. In step 40 when the first pixel considered is closer to the X axis than the third pixel considered, the testing is occurring downwardly on the right side of the perimeter 13. Accordingly, in accordance with the matrix of FIG. 7, two D2 motions are provided to the CPU 22. Thus, the corrective motions provided at step 41 and/or 42 prevent a single pixel, such as pixel 33 in FIG. 3, from being identified as a blemish.

Returning to step 39, when the horizontal positions of the first and third pixels are not the same, step 43 is entered and the horizontal positions of the first and fourth pixels are compared. When the first and fourth pixels have the same horizontal value, a pattern such as those shown in FIGS. 5c and 5d has been located. Step 44 is then entered to compare the vertical positions of the first and fourth pixels, and when the first pixel is further from the X axis than the fourth pixel, the motion is upwardly and three D6 pixel motions are provided at step 46. When the first pixel is closer to the X axis than the fourth pixel, the motion is downward and step 45 is entered and three D2 pixel motions are provided to the CPU 22. Step 37 is then reentered for consideration of the next five pixels. Thus, the identification of two adjacent pixels such as 34 and 35 of FIG. 3 as a blemish is avoided, irrespective of the location of the adjacent pixels on the perimeter 13.

Returning to step 43, when the horizontal positions of the first and fourth pixels are not the same, step 47 is entered to compare the horizontal positions of the first and fifth pixels. When the first and fifth pixels have different horizontal values, the motion can be either around a corner or along the horizontal axis and step 49 is entered to begin the horizontal investigation. At step 47, when the first and fifth pixels have the same horizontal position, step 48 is entered and the horizontal positions of the second, third and fourth pixels are compared to determine whether or not whether one of the patterns of FIGS. 5e and 5f is present. When such a pattern is not indicated, the motion is either around a corner or along the horizontal axis and step 49 is entered. When at step 48 the second, third and fourth pixels have the same horizontal position, one of the patterns shown in FIGS. 5e and 5f has been located and step 50 is entered to compare the vertical positions of the first and fifth pixels. When the first pixel is further from the X axis than the fifth pixel, the motion is upwardly and step 52 is entered to provide four D6 motions to the CPU 22. When the motion is downward, four D2 motions are input at step 51. Thus, the identification of three adjacent pixels, such as 30, 31 and 32, as a blemish is avoided. Step 37 is reentered and the next succeeding five pixels, the first four of which were included in the preceding five, are input and the method repeated.

Figure 6E:
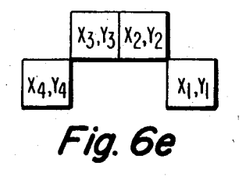
Figure 6F:
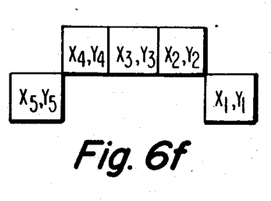
Figure 8B:
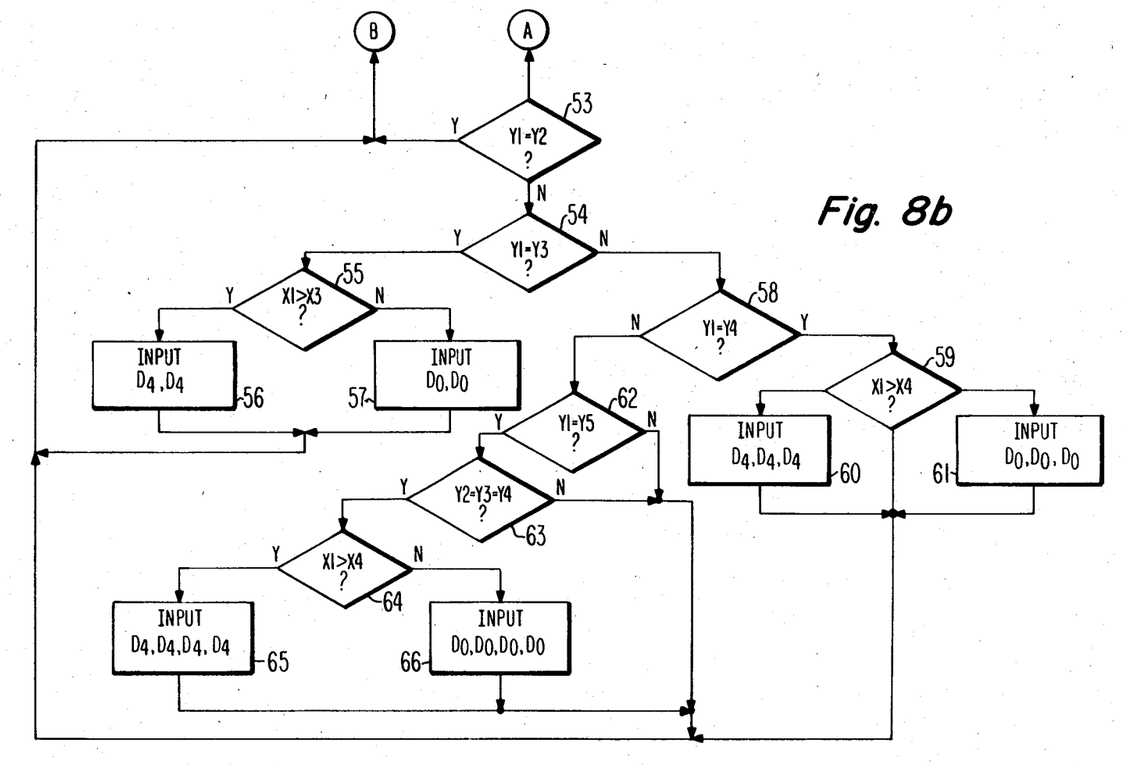

FIG. 8b is a flow chart of the method of investigating the motions in the horizontal direction along the top and bottom of the perimeter 13. In step 53, the horizontal positions of the first two pixels are compared. When these positions are the same, step 37 of FIG. 8a is reentered and the next five pixels are input. When the horizontal positions of the first two pixels are different, step 54 is entered to compare the horizontal positions of the first and third pixels. When the horizontal positions are the same, a pattern of the type shown in FIGS. 6a and 6d has been indicated and step 55 is entered to determine whether or not the motion is to the left or to the right along the perimeter 13. When $X_1$ is closer to the Y axis than $X_3$, the motion is to the right, and step 56 is entered and two D0 pixel motions are provided. When the motion is to the left, step 56 is entered and two D4 motions are provided. At step 54, when the horizontal positions of the first and third pixels are not the same, step 58 is entered to compare the horizontal positions of the first and fourth pixels. When the vertical positions are the same, a pattern of the type shown in FIGS. 6b and 6e is present and step 59 is entered to determine whether the motion is to the right or to the left. When the motion is to the left, step 60 is entered and three D4 pixel motions are provided. When the motion is to the right, step 61 is entered and three D0 pixel motions are provided.

Returning to step 58, when the first and fourth pixels have different vertical positions, step 62 is entered to compare the vertical positions of the first and fifth pixels. When the positions are different, no correction of the pixel motions is required and the procedure returns to step 37 of FIG. 8a. At step 62, when the horizontal positions are the same, step 63 is entered to compare the positions of the second, third and fourth pixels to determine whether or not one of the patterns of 6c or 6f is present. When no such pattern is present, the procedure returns to step 37 of FIG. 8a. When such a pattern has been detected, step 64 is entered to determine whether the motion is to the left or to the right. When the motion is to the left, step 65 is entered and four D4 pixel motions are provided. When the motion is to the right, step 66 is entered and four D0 motions are provided.

With the invention, the identification of permissible perimeter variations as perimeter adjacent blemishes is avoided by providing straight pixel motions in place of diagonal pixel motions. The permissible variations are identified by sequentially considering a plurality of adjacent pixels. Diagonal pixel motions are recorded as straight pixel motions when the first and last pixel motions are diagonal in opposite directions and all, if any, intervening pixel motions are straight. The diagonal pixel motions occur when the first and last pixels of the selected plurality have the same position with respect to one of the axes and the remaining pixels all have a position with respect to the same axes which is different from the first and last pixels but is the same for the remaining pixels. At least three pixels must be considered because two pixel motions are needed to identify the permissible variations. A maximum of five pixels must be considered because any diagonal pixel motion which is followed by three straight pixel motions cannot be identified as a blemish.

What is claimed is:

1. A method of avoiding the identification of permissible variations in the perimeter of an image on a CCD (charge coupled device) as blemishes in the proximity of said perimeter comprising the steps of:

detecting the charge levels of perimeter identifying pixels in a sequence of pixel motions, wherein a pixel motion is the detection of adjacent pixel charge levels and wherein adjacent pixels are pixels having contiguous sides or contiguous corners, said pixel motions being taken in directions defined by a pixel direction matrix wherein the pixel being detected is surrounded by adjacent pixels whereby the detection of side adjacent pixels results in straight pixel motions and the detection of corner adjacent pixels results in diagonal pixel motions; and:

further including the step of sequentially detecting the charge levels on a plurality of adjacent pixels and recording diagonal pixel motions as straight pixel motions where the first and the last pixel motions are diagonal in opposite directions and all intervening pixel motions are straight.

2. The method of claim 1 wherein said plurality includes at least three pixels.

3. The method of claim 1 wherein said plurality includes a maximum of five pixels.

4. The method of claim 2 wherein said plurality includes a maximum of five pixels.

5. The method of claim 1 wherein said pixel being detected is adjacent to eight pixels whereby four straight pixel directions and four diagonal pixel directions are defined.

6. The method of claim 5 wherein said pixel being detected is sequentially moved along said perimeter identifying pixels and said pixel direction matrix follows said pixel being detected.

7. The method of claim 4 wherein said pixel being detected is adjacent to eight pixels whereby four straight pixel directions and four diagonal pixel directions are defined.

8. The method of claim 7 wherein said pixel being detected is sequentially moved along said perimeter identifying pixels and said pixel direction matrix follows said pixel being detected.

9. The method of claim 3 wherein said pixel being detected is adjacent to eight pixels whereby four straight pixel directions and four diagonal pixel directions are defined.

10. The method of claim 9 wherein said pixel being detected is sequentially moved along said perimeter identifying pixels and said pixel direction matrix follows said pixel being detected.

11. A method of avoiding the identification of permissible variations in the perimeter of an image on a CCD (charge coupled device) as blemishes in the proximity of said perimeter comprising the steps of:

detecting the charge levels of perimeter identifying pixels in a sequence of pixel motions, wherein a pixel motion is the detection of adjacent pixel charge levels and wherein adjacent pixels are pixels having contiguous ends or contiguous corners, said pixel motions being taken in directions defined by a pixel direction matrix wherein the pixel being detected is surrounded by adjacent pixels whereby the detection of said adajcent pixels results in straight pixel motions and the detection of corner adjacent pixels results in diagonal pixel motions;

selecting a number of pixels for detection, sequentially detecting the charge level on said pixels along a horizontal axis lying along a horizontal side of said perimeter, comparing the pixel location with respect to a vertical axis lying along a vertical side of said perimeter by individually comparing the vertical location of the first pixel with the vertical locations of the other pixels in said plurality, recording diagonal pixel motions as straight pixel motions when the first and last pixels of said plurality have a first vertical position and the other pixels of said plurality have a second vertical position; and repeating said sequential consideration along said vertical axis and comparing pixel locations with respect to said horizontal axis, and recording diagonal pixel motions as straight pixel motions when the first and last pixel of said plurality have a first horizontal position and the other pixels have a second horizontal position.

12. The method of claim 11 wherein said plurality includes at least three pixels.

13. The method of claim 11 wherein said pixel being detected is adjacent to eight pixels whereby four straight pixel directions and four diagonal pixel directions are defined.

14. The method of claim 12 wherein said plurality includes a maximum of five pixels.

15. The method of claim 13 wherein said pixel being detected is sequentially moved along said perimeter identifying pixels and said pixel direction matrix follows said pixel being detected.

16. The method of claim 14 wherein said pixel being detected is adjacent to eight pixels whereby four straight pixel directions and four diagonal pixel directions are defined.

17. The method of claim 16 wherein said pixel being detected is sequentially moved along said perimeter identifying pixels and said pixel direction matrix follows said pixel being detected.

18. The method of claim 13 wherein said pixel being detected is adjacent to eight pixels whereby four straight pixel directions and four diagonal pixel directions are defined.

19. The method of claim 18 wherein said pixel being detected is sequentially moved along said perimeter identifying pixels and said pixel direction matrix follows said pixel being detected.

* * * * *